United States Patent
Pendl et al.

[11] Patent Number: 5,817,153
[45] Date of Patent: Oct. 6, 1998

[54] METHOD OF PHOTO-OXIDATIVE TREATMENT OF TISSUES CONTAINING COLLAGEN

[75] Inventors: Roger Pendl, Guntershausen; Werner Müller-Glauser, Wiesendangen; Peter Bittmann, Zürich, all of Switzerland

[73] Assignee: Sulzer Innotec AG, Winterthur, Switzerland

[21] Appl. No.: 729,259

[22] Filed: Oct. 9, 1996

[30] Foreign Application Priority Data

Oct. 11, 1995 [EP] European Pat. Off. .............. 95810637

[51] Int. Cl.$^6$ ..................................................... A61L 17/00
[52] U.S. Cl. ................................. 8/94.11; 8/94.18; 8/404; 204/157.68; 623/13; 623/16; 623/11
[58] Field of Search .................... 8/94.11, 94.18, 8/94.33, 404; 204/157.68; 623/13, 16, 11

[56] References Cited

U.S. PATENT DOCUMENTS

| | | | |
|---|---|---|---|
| 3,152,976 | 10/1964 | Kuntz | 8/94.18 |
| 5,147,514 | 9/1992 | Mechanic | 204/157.68 |
| 5,409,479 | 4/1995 | Dew et al. | 606/9 |

FOREIGN PATENT DOCUMENTS 0 411 925 A2  2/1991  European Pat. Off. .

OTHER PUBLICATIONS

Ramshaw, John A.M., et al. (1994) "Methylene blue sensitized photooxidation of collagen fibrils", *Biochimica et Biophysica Acta*, 1206(2):225–230 (Month Unknown).

Moore, M.A., et al. (1994) "Stabilization of pericardial tissue by dye–mediated photooxidation", *Journal of Biomedical Materials Research*, 28(5):611–618 (Month Unknown).

*Primary Examiner*—Alan Diamond
*Attorney, Agent, or Firm*—Townsend and Townsend and Crew LLP

[57] ABSTRACT

In the method of a photo-oxidative treatment of tissue containing collagen tissue, the tissue is pre-treated with an aqueous conditioning solution prior to an irradiation with light. In this pre-treatment the tissue permeable to the solution is loaded with a dye contained in the solution, in particular with methylene blue. This dye, activated by light, catalyzes photo-oxidative reactions. In accordance with the invention a substance is added to the conditioning solution, the refractive index of which is greater than that of water. As a result of this additive, the tissue containing collagen assumes a greater transparency for light during the pre-treatment.

13 Claims, 2 Drawing Sheets

METHOD OF PHOTO-OXIDATIVE TREATMENT OF TISSUES CONTAINING COLLAGEN

BACKGROUND OF THE INVENTION

The invention relates to a method of photo-oxidative treatment of tissues containing collagen. Tissues containing collagen are, for example, cartilage tissue and tissue from ligaments or tendons. The invention relates to tissue of the kind which has been prepared in accordance with the method of the invention.

A photoxidative treatment of tissue containing collagen (in particular pericardial tissue) is known from U.S. Pat. No. 5,147,514. In this method tyrosine, tryptophane and/or histidine radicals from collagenous fibers react with oxygen under the catalytic effect of dye molecules activated by light in such a manner that bonds form between collagenous fibers. Methylene blue, methylene green, Bengal pink, riboflavine, proflavine, fluorescein, eosin and pyridoxal-5-phosphate are named as effective dyes.

Cartilage tissue is—apart from individually occurring chondrocytes—made up of a network of collagenous fibers and high molecular proteoglycane. The tissue is made up of about 75% water. On the basis of this composition, the cartilage is a soft, elastic, open-pored and permeable tissue. Water which is located in the tissue is easily exchangeable with the water from the surroundings. An exchange of water or of substances dissolved in the water can, other than by diffusion, also take place by convection, which is associated with volume changes by means of compression and expansion of the tissue. Good exchangeability is a prerequisite for a conditioning of the cartilage tissue and the loading thereof with a dye. These statements also apply to tendons and ligaments.

The known method is used in the photo-oxidative treatment of tissue obtained from pericardia, which is provided for the manufacture of implantable cardiac valves. This tissue is areal and thin-walled—around 0.5 mm thick—and can be exposed from both sides.

The fact that collagenous fibers are altered through the photo-oxidative treatment can be proved by means of collagenase. This enzyme dissolves the fibers of the untreated tissue into parts, with the result that the mechanical consistency of the tissue is lost. Following a photo-oxidative treatment, this "digestion" by means of collagenase is no longer effective to the same extent.

The collagenous fibers are partially cross-linked with one another by means of the photo-oxidative treatment, by means of which the tissue gains a greater ability to withstand mechanical loading. Moreover, under the catalytic effect of the dye, collagenous fibers are photo-oxidately altered in a manner so that when the treated tissue is used as an implant, immunological defense reactions do not occur or are only slight.

The wish exists—analogue to heart valves or pericardia—of being able to use cartilage preparations as implants for the surgical treatment of knee joints. Joint cartilages are 2 to 3 mm thick and grown on bone. To be useful as an implant, the cartilage tissue should be used together with a piece of associated bone material. This means that the tissue can only be exposed from the side of the exposed surface. Thus the light has to be able to penetrate the tissue up to 3 mm depth. As experiments have shown, however, the transparency to light is rather poor.

SUMMARY OF THE INVENTION

It is therefore the object of the invention to produce a method which makes possible a photo-oxidative treatment of the collagen network, despite poor transparency to light of the natural cartilage tissue.

The collagenous fibers and the proteoglycane form a plurality of scattering centers, due to which the light can only effectively penetrate into the marginal areas of the cartilage tissue. The light scatter is caused by the fact that the refractive index of the scattering centers differs greatly locally. The teaching of the invention is therefore based on the idea of raising the refractive index of the water which fills the space between the scattering centers, by addition of suitable substances, so that values of the refractive index are levelled out in the tissue. Additives, which may be used for this purpose, are, for example, diethyleneglycol (refractive index n=1.447 at 20° C.) or glycerine (n=1.474).

In the method in accordance with the invention for a photo-oxidative treatment of collagenous tissues, the tissue is pre-treated with an aqueous conditioning solution prior to irradiation with light. In this pre-treatment the tissue which is permeable for the solution is loaded with a dye contained in the solution, in particular with methylene blue. This dye, activated by light, catalyzes photo-oxidative reactions. In accordance with the invention, a substance is added to the conditioning solution, the refractive index of which is larger than that of water (n=1.333 at 25° C.). As a result of this additive, the collagenous tissue assumes greater transparency to light in the pre-treatment.

The photo-oxidative treatment is carried out in accordance with the following three-step method, wherein the temperature is preferably maintained at about 14° to 18° C.

1. Pre-treatment of the collagenous tissue with the conditioning solution for about 1 to 5 hours.

2. Exposure of the collagenous tissue for about 10 to 50 hours.

3. Decolorization of the collagenous tissue as well as removal of the additive by repeated washing with a decolorizing solution.

DESCRIPTION OF THE PREFERRED EMBODIMENTS

Figure 1:
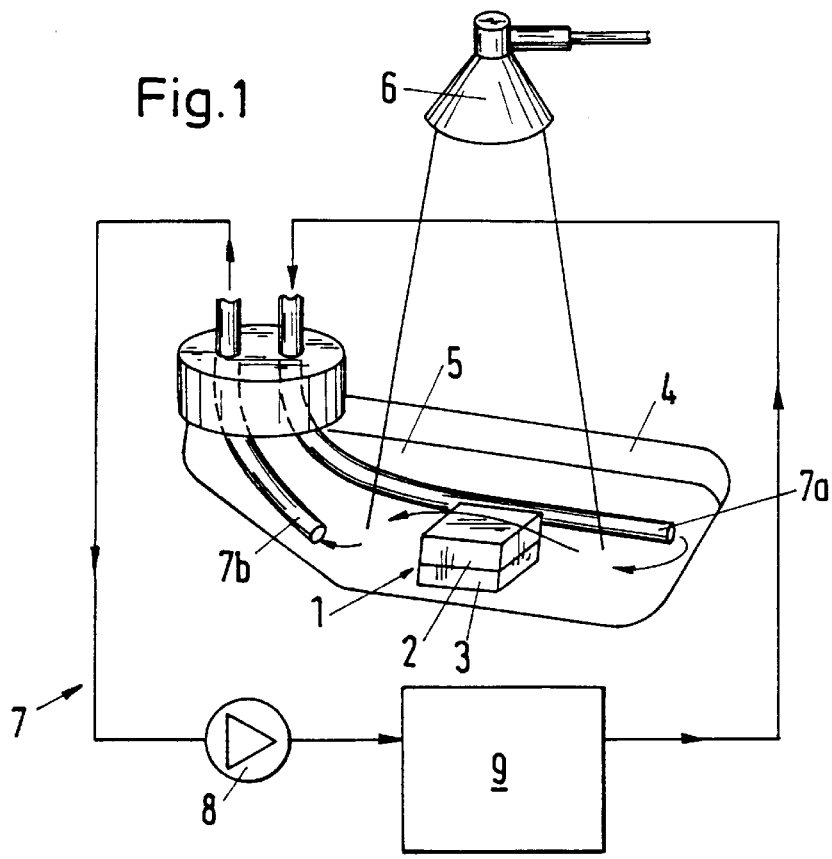
FIG. 1 is a schematic view illustrating an experimental arrangement for the carrying out of a photo-oxidative treatment.

The experimental arrangement of FIG. 1 shows a preparation 1 with a cartilage layer 2 and a bone layer 3, which is flushed around and over by a solution 5 in a transparent, closed container 4. The preparation 1 is exposed by a lamp 6 (cold light halogen lamp, 75 W, 12 V, 10° angle of beam). The solution 5 is circulated in the circuit 7 by a peristaltic pump 8 and kept at a pre-given temperature (16° C.) in a refrigeration device 9. The solution is moved into or out of the container 4 via the hose pieces 7a and 7b. The solution 5 is, as a rule, the conditioning solution with which the preparation 1 has been pre-treated prior to exposure. A ligament or a tendon can also be provided in place of the cartilage preparation 1.

The solution 5 is made up of a phosphate buffer according to Sorensen which comprises, glycerine ($C_3H_8O_3$, molecular weight M=92 g/mol) and methylene blue ($C_{16}H_{18}ClN_3S.3H_2O$, M=320 g/mol+aq). The phosphate buffer according to Sorensen has a molarity of 1/15 and a pH value of 7.4; it is a solution of pure water ("Nanopur") and 1.787 g/l potassium hydrogen phosphate ($KH_2PO_4$, M=136 g/mol) and also 9.532 g/l disodium hydrogen phosphate ($Na_2HPO_4$, M=178 g/mol). The choice of methylene blue as a dye is particularly advantageous, since this substance is not toxic (as can be proved by means of various uses in medicine). A proportion is advantageously provided of about 30% volume for the glycerine and of 0.01% by weight for the methylene blue.

Preparations 1 are, for example, taken from the shoulder joints of slaughtered cattle, wherein pieces of cartilage with bone (approximately 10×10×5 mm) are cut out of the joints by means of an oscillating saw known from surgery.

The preparations 1 are transported in a buffer solution and also stored and kept cool thereby (at about 4° C.).

During the photo-oxidation, dye molecules are put into an excited state by photons of the irradiating light. In this state they can react with oxygen or water to form an intermediate product. While the intermediate product reacts with traces of amino acid of the collagen (or other proteins), the dye is released unchanged: it has the effect of a catalyzator in the photo-oxidation process.

Nevertheless, irreversible changes of the dye molecules also occur under the influence of the light, which appear as a fading of the dye. Provision must be made for the continuous supply of dye molecules in the tissue. This takes place by the preparation 1 being constantly flushed in conditioning solution 5 during the exposure. A partial renewal of the dye in the tissue results by an exchange of material between the tissue and the solution 5, wherein bleached-out dye is replaced by intact dye. Occasionally—in each case after approximately 24 hours—the entire reaction solution has to be replaced with a fresh one.

Photo-oxidation is slowed down at lower temperatures, and the collagenous tissue can be damaged by the effect of heat at higher temperatures. Light is absorbed and transformed into heat by means of the dye. The photo-oxidation is an exothermic reaction. Therefore the circulated solution 5 has to be cooled constantly—in order to be able to carry out the treatment at an optimum temperature between about 14° and 18° C.

During photo-oxidation, hydrogen ions are set free. Therefore it is necessary—in order to be able to carry out the treatment at an optimal pH value between about 7 and 8—that a buffer solution be used (phosphate buffer according to Sorensen).

Oxygen is used during photo-oxidation. The content of oxygen, which is normally contained in the reaction solution, suffices as a rule. Injection of additional oxygen does not bring about any improvement of the treatment method.

Methylene blue is advantageously used with a concentration of 0.01% by weight. If a weaker concentration is used, the photo-oxidative treatment is too slow. If a greater concentration is used, too much light is absorbed into the reaction solution and into the outer regions of the tissue, so that the entire tissue and in particular its deeper regions receive too little light.

Due to the relatively small molecular weight of methylene blue (M=320 g/mol) this dye diffuses well into and through the collagenous tissue. This is confirmed by examinations on microsections.

Figure 2:
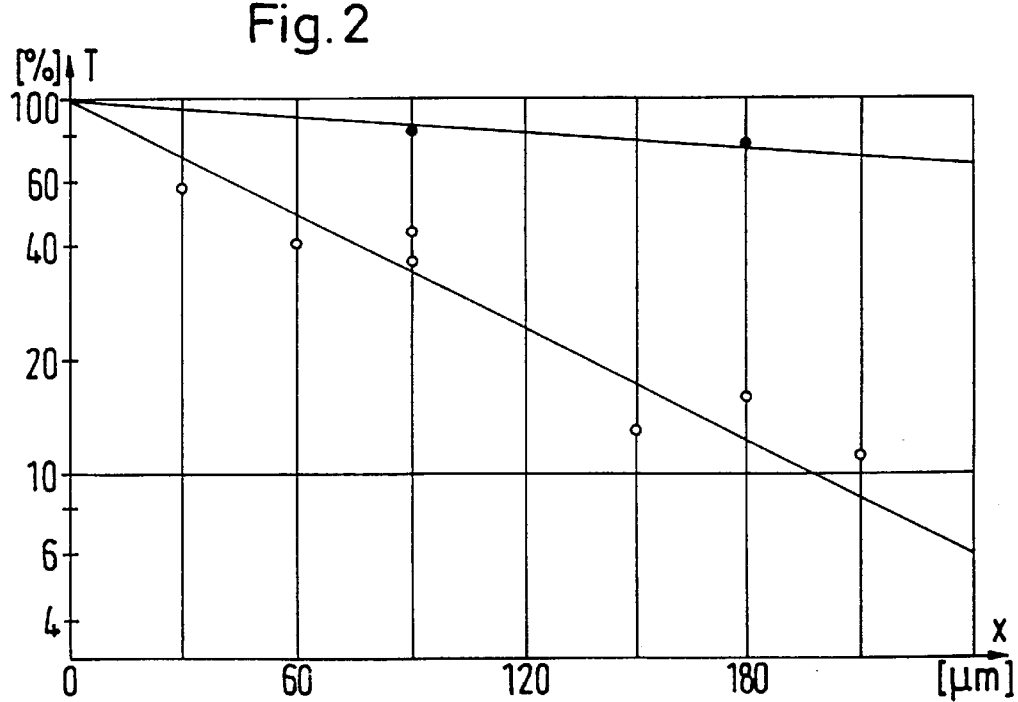
FIG. 2 is a diagram illustrating transmission of collagenous tissues as a function of the thickness of the tissue.

The transmission of the collagenous tissue is determined at the maximum absorption of methylene blue, namely 665 nm. To this end, microtome sections with thicknesses between 30 and 210 μm are prepared. Test results are shown in the diagram of FIG. 2. T is the transmission and x the thickness of a measured section. The values for T are recorded in a logarithmic scale. The empty circles give the measurement values for cartilage tissue, which has to be pre-treated in accordance with the known method. The filled circles show the corresponding values for pre-treated tissue in accordance with the invention, whereas glycerine has been used as an additive with a proportion a of 80% by volume.

Figure 3:
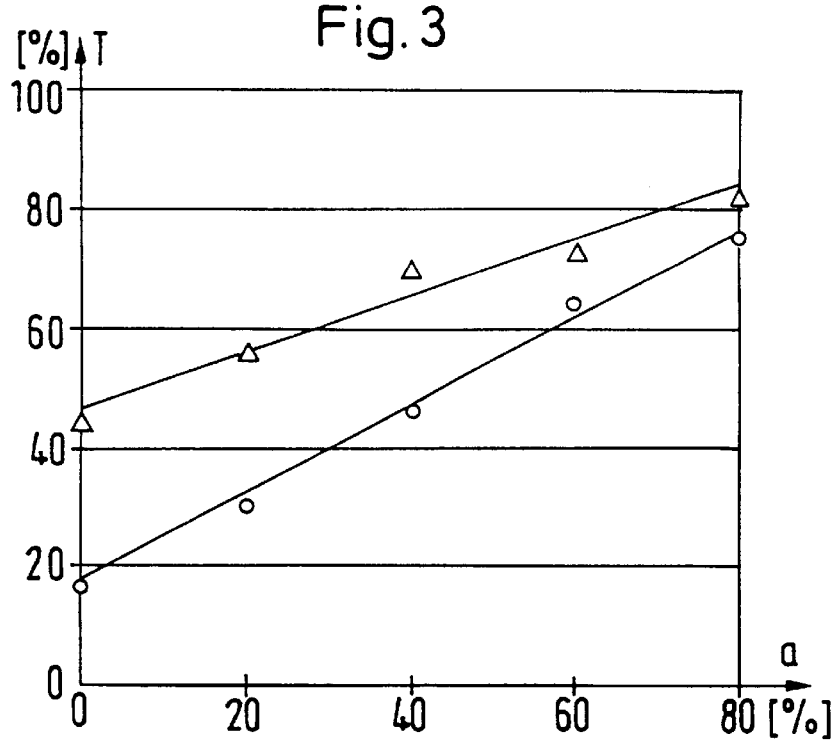
FIG. 3 is a diagram illustrating transmission of tissues following pre-treatments with conditioning solutions which contain glycerine.

FIG. 3 shows how the transmission T depends on the proportion of glycerine a. The two measurement series shown relate to layer thicknesses of 90 μm (triangles) and 180 μm (circles).

As is seen from the diagrams in FIGS. 2 and 3, a considerable improvement in the transparency of the tissue results from the pre-treatment in accordance with the invention. The light penetration depth can be enlarged by at least five times. Thus the photo-oxidative treatment of joint cartilage becomes possible.

After the carrying out of the photooxidation, the collagenous tissue is decolorized and, simultaneously, the additive is removed. This happens by means of repeated washing with a decolorizing solution. The decolorizing solution of the above-named phosphate buffer according to Sorensen is used with advantage. In order to increase the solubility of the dye, up to 50% volume of ethanol can be added to this phosphate buffer.

Figure 4:
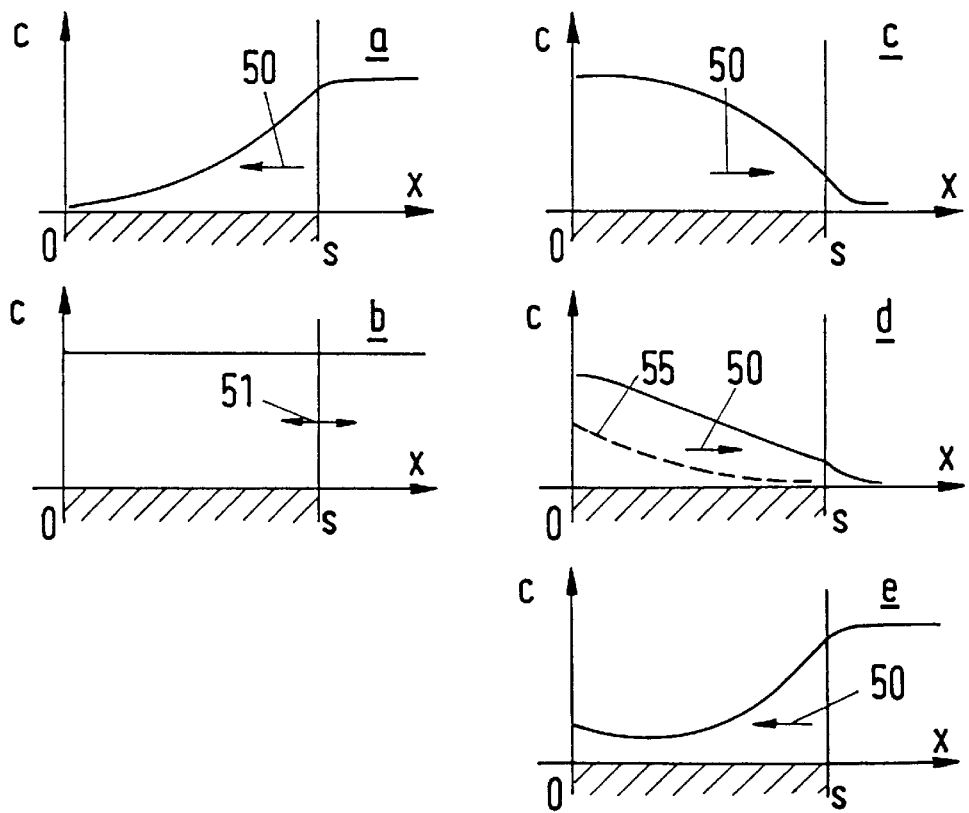
FIG. 4 shows diagrams for the qualitative representation of the dye dispersion in the tissue.

On the basis of the diagrams of the partial figures a to e in FIG. 4, a few more aspects of the tissue coloring should be explained. The diagrams illustrate the dye concentration c as a function of x. The distance from the bone surface (x=0) is given by x. The cartilage tissue extends over the interval 0<x<s. The reaction solution or the decolorization solution is located in the region x>s.

FIG. 4a illustrates the preliminary phase of the coloring during the pre-treatment. The arrow 50 indicates the dye transport due to diffusion. Following completed pre-treatment, an equilibrium should exist with a homogenous distribution of dye. This is illustrated in FIG. 4b. The double arrow 51 shows that a material exchange is further taking place over the tissue surface at x=s, by means of which a replacement for bleached-out dye molecules in the tissue takes place.

FIGS. 4c and 4d illustrate the decolorization following photo-oxidation. Since during the decolorization, the concentration of dye is still relatively high in the deeper regions of the tissue for some time, the exposure can be advantageously continued during this method phase and, what is more, up to a point in time where the concentration c takes on for example the curve 55 which is drawn with a broken line. This is advantageous, because the photo-oxidation has previously been far less effective in the deeper regions than in the upper regions.

The teaching, of continuing the exposure during the decolorization as well, may be further developed to an advantageous method variation. The exposure should be undertaken intermittently, namely in such a way that during the exposure phases the cartilage tissue is simultaneously decolorized and during intermediate phases the cartilage tissue is treated with conditioning solution without exposure and colored once again. A renewed coloring of the tissue is illustrated by the diagram of FIG. 4e.

If it is intended to use photo-oxidatively treated cartilage tissue as an implant, then the treatment of the tissue should be carried out to such an extent that the collagenous fibers change in such a manner that immunological defense reactions do not occur in a patient, or are only slight. Moreover, the cartilage tissue ought to gain a greater mechanical loadability as a result of the photo-oxidative treatment.

In the exposure of cartilage preparations, the exposure can only be effectively undertaken from one side. In the treatment of ligaments and tendons in accordance with the invention an exposure from both or all sides is possible.

We claim:

1. A method of photo-oxidation treatment of a tissue containing collagen, using an aqueous conditioning solution to which the tissue is permeable and which includes a dye and an additive that is greater in refractive index than water, the method comprising the steps of subjecting the tissue to the aqueous conditioning solution containing the dye and additive for a sufficient period of time to produce a greater transparency of the tissue sufficient for irradiation of the light for photo-oxidation; irradiating the tissue with the light intermittently with alternating irradiation phases during irradiation of the tissue and intermediate phases therebetween; rinsing the tissue in an oxygen-containing decolorizing solution during the irradiation phases; and rinsing the tissue in an oxygen-containing conditioning solution during the intermediate phases.

2. The method of claim 1, wherein the step of subjecting the tissue to the aqueous conditioning solution comprises subjecting the tissue to a solution containing glycerine.

3. The method of claim 1, wherein the step of subjecting the tissue to the aqueous conditioning solution comprises subjecting the tissue to a solution containing methylene blue dye.

4. The method of claim 1, wherein the steps of subjecting and irradiating comprise subjecting the tissue to the aqueous conditioning solution containing the dye and additive and irradiating the tissue with the light in presence of oxygen to produce catalytic effect of the dye to photo-oxidatively alter collagenous fibers of the tissue to minimize immunological defense reactions when used as an implant in a human body.

5. The method of claim 4, wherein the step of irradiating comprises irradiating the tissue with the light in the presence of oxygen for a sufficient period of time to crosslink at least partially the collagenous fibers to provide the tissue with a greater ability to withstand mechanical loading.

6. The method of claim 1, wherein the step of subjecting comprises subjecting the tissue to the aqueous conditioning solution containing the dye and additive for around 1 to 5 hours.

7. The method of claim 1, wherein the step of irradiating comprises irradiating the tissue with the light intermittently for around 10 to 50 hours.

8. The method of claim 1, further comprising the steps of decolorizing the tissue and removing the additive from the tissue by repeated washing with a decolorizing solution.

9. The method of claim 1, wherein the further steps of decolorizing the tissue and removing the additive comprise repeatedly washing the tissue with a phosphate buffer decolorizing solution which comprises 0 to 50% by volume ethanol with a molar concentration of $1/15$ and a pH value of about 7.4.

10. The method of claim 1, wherein the step of rinsing the tissue comprises pumping and circulating the oxygen-containing conditioning solution to the tissue and cooling the oxygen-containing conditioning solution.

11. The method of claim 1, wherein the step of subjecting the tissue to the aqueous conditioning solution containing the dye and additive comprises subjecting the tissue to a solution having a mixture of about 30% by volume of glycerine and a phosphate buffer which has a molar concentration of $1/15$ and a pH value of 7.4, and methylene blue of 0.01% by weight.

12. A method of pre-treating a tissue containing collagen in a photo-oxidative treatment process that employs irradiation with a light to raise the refractive index of the tissue prior to irradiation of the tissue, using a solution that includes a mixture of about 30% by volume of glycerine and a phosphate buffer which has a molar concentration of $1/15$ and a pH value of about 7.4, and methylene blue of 0.01% by weight, the method comprising the step of subjecting the tissue to the solution for a sufficient period of time to produce a greater transparency of the tissue.

13. A method of pre-treating a tissue containing collagen in a photo-oxidative treatment process that employs irradiation with a light only in a direction across a thickness to raise the refractive index of the tissue through the thickness prior to irradiation of the tissue, using an aqueous conditioning solution to which the tissue is permeable and which includes a dye and an additive that is greater in refractive index than water, the method comprising the step of subjecting the tissue to the aqueous conditioning solution containing the dye and additive for a sufficient period of time to produce a greater transparency of the tissue across the thickness sufficient for irradiation of the light for photo-oxidation, wherein the step of subjecting the tissue to the aqueous conditioning solution containing the dye and additive comprises subjecting the tissue to a solution having a mixture of about 30% by volume of glycerine and a phosphate buffer which has a molar concentration of $1/15$ and a pH value of about 7.4, and methylene blue of 0.01% by weight.

* * * * *